United States Patent [19]

Pawelek et al.

[11] Patent Number: 5,523,077
[45] Date of Patent: Jun. 4, 1996

[54] COMPOSITION AND METHOD FOR WHITENING SKIN

[75] Inventors: John M. Pawelek, Hamden; Jean L. Bolognia, North Haven; Michael P. Osber, Hamden; Stefano A. Sodi, New Haven, all of Conn.

[73] Assignee: Yale University, New Haven, Conn.

[21] Appl. No.: 104,968

[22] Filed: Aug. 10, 1993

Related U.S. Application Data

[63] Continuation-in-part of Ser. No. 882,094, Feb. 6, 1992, abandoned.

[51] Int. Cl.$^6$ ............................... A61K 7/42; A61K 7/48
[52] U.S. Cl. ................................ 424/62; 424/59
[58] Field of Search ........................ 424/62, 59

[56] References Cited

U.S. PATENT DOCUMENTS

| | | | |
|---|---|---|---|
| 4,678,663 | 7/1987 | Scott | 424/62 |
| 4,742,066 | 5/1988 | Deckner | 514/311 |
| 4,769,382 | 9/1988 | Dubur | 514/356 |
| 4,818,521 | 4/1989 | Tamabuchi | 424/62 |
| 4,927,762 | 5/1990 | Darfler | 435/240.25 |
| 4,985,241 | 1/1991 | Zimmerman | 424/85.2 |
| 5,091,385 | 2/1992 | Guilliya | 514/638 |
| 5,140,043 | 8/1992 | Darr | 514/474 |
| 5,262,153 | 11/1993 | Mishima | 424/62 |

FOREIGN PATENT DOCUMENTS

| | | |
|---|---|---|
| 0269017 | 6/1988 | European Pat. Off. |
| 2152442 | 4/1973 | France |
| WO85/04101 | 9/1985 | WIPO |

OTHER PUBLICATIONS

Griffith et al., 1979, "Translocation of Intracellular Glutathiae to Membrane-Bound γ-glutamyl transpeptidase as a discrete step in the γ-glutamyl cycle: Glutathionuria after Inhibition of Transpeptidase", Proc. Natl. Acad. Sci. USA 76:268–272.

Meiser, 1991, "Glutathione Deficiency Produced by inhibition of its Synthesis and its reversal Applications in Research and Therapy," Pharmac. Ther. 51:155–194.

Seelig et al., 1984, "γ-Glutamylcysteine Synthetase, Interactions of an Essential Sulphydryl Group," J. Biol. Chem. 259:3534–3538.

Griffith et al., 1977, "Inhibition of γ-Glutamylcysteine Synthetase by Cystamine: An Approach to a Therapy of 5-Oxyprolinuria," Biochemical and Biophysical Res. Comm. 79:919–925.

S. T. N., Serveur de Bases de Données, Karlsruhe, DE, Fichier Chemical Abstracts, vol. 115, No. 109447, 1991.

International Search Report in connection with the PCT Application No. PCT/US93/02113.

Korner et al., 1982, "Mammalian Tyrosinase Catalyzes Three Reactions in the Biosynthesis of Melanin", Science 217:1163–1165.

Bolognia et al., 1989, "UVB-Induced Melanogenesis May Be Mediated Through the MSH-Receptor System", J. Invest. Dermatol. 92:651–656.

Chakraborty et al., 1991, "Structural/Functional Relationships Between Internal and External MSH Receptors: Modulation of Expression in Cloudman Melanoma Cells by UVB Radiation", J. Cell. Phys. 147:1–6.

Kosower, E. M., 1976, "Chemical Properties of Glutathione, in Glutathione Metabolism and Function", ed I. M. Arias and W. B. Jakoby, Raven Press, NY, pp. 1–15.

Meister et al., 1983, "Glutathione", Ann. Rev. Biochem. 52:711–60.

(List continued on next page.)

Primary Examiner—Thurman K. Page
Assistant Examiner—Sally Gardner
Attorney, Agent, or Firm—Pennie & Edmonds

[57] ABSTRACT

A skin-whitening and suntan-inhibiting composition comprising (a) a compound which depletes glutathione, and (b) hydroquinone or an alkyl or aralkyl ether of hydroquinone.

9 Claims, 3 Drawing Sheets

CONTROL    MSH/MIX    HQ (10-6M)    CYS (10-5M)    HQ/CYS

OTHER PUBLICATIONS

Griffith et al., 1979, "Translocation of intracellular glutathione to membrane–bound γ–glutamyl transpeptidase as a discrete step in the γ–glutamyl cycle: Glutathionuria after inhibition of transpeptidase", *Proc. Natl. Acad. Sci.* 76:268–272.

Tyrrell et al., 1988, "Correlation between Endogenous Glutathione Content and Sensitivity of Cultured Human Skin Cells to Radiation at Defined Wavelengths in the Solar Ultraviolet Range", *Photochemistry Photobiology* 47:405–412.

Tyrrell et al., 1986, "Endogenous Glutathione Protects Human Skin Fibroblasts Against the Cytotoxic Action of UVB, UVA and Near–Visible Radiations, Photochemistry and Photobiology", 44:561–564.

Hanada et al., 1991, "Effect of Glutathione Depletion on Sunburn Cell Formation in the Hairless Mouse", *J. Invest. Dermatol.* 96:838–840.

Thrall et al., 1991, "Effect of L–Dopa Methylester and Glutathione Depletion on Murine B16BL6 Melanoma Growth in Vitro", *J. Invest. Dermatol.* 97:1073–1077.

Prezioso et al., 1990, "Effects of Tyrosinase Activity on the Cytotoxicity of 3,4–Dihydroxybenzylamine and Buthionine Sulfoximine in Human Melanoma Cells", *Pigment Cell Research* 3:49–54.

Alena et al., 1991, "Enhancement of the In Vivo Antimelanoma Effect of N–Acetyl–4–S–Cysteaminylphenol by Combination with Butathione Sulfoximine", *3rd Meeting PASPCR*, Edmonton, Canada.

Hochstein et al., "The Cytotoxicity of Melanin Precursors", *New York Academy of Sciences,* 876–886.

Lerner, A. B., 1971, "On the Etiology of Vitiligo and Gray Hair", *Am. J. Med.* 51:141–147.

Pawelek et al., 1973, "Molecular Biology of Pigment Cells, Molecular Controls in Mammalian Pigmentation", *Yale J. Biol. Med.* 46:430–443.

Pawelek, J. M., 1976, "Factors Regulating Growth and Pigmentation of Melanoma Cells", *J. Invest. Dermat.* 66:201–209.

Pawelek et al., 1978, "5,6–Dihydroxyindole is a melanin precursor showing potent cytotoxicity", *Nature* 276:627–628.

Proc. Natl. Acad. Sci. USA, vol. 76, No. 1, pp. 268–272, Jan. 1979 Translocation of Intracellular Glutathione to Membrane–Bound γ–Glutamyl Transpeptidase as a Discrete Step in the γ–Glutamyl Cycle: Glutathionuria After Inhibition of Transpeptidase.

Glutathione Deficiency Produced by Inhibition of its Synthesis, and its Reversal Applications in Research and Therapy, Pharmac. Ther. vol. 51, pp. 155–194, 1991.

γ–Glutamylcysteine Synthetase, Interactions of an Essential Sulfhydryl Group The Journal of Biological Chemistry, vol. 259, No. 6, Issue of Mar. 25, pp. 3534–3538, 1984.

Biochemical and Biophysical Research Communications, vol. 79, No. 3, 1977 Inhibition of –Glutamylcysteine Synthetase by Cystamine: An Approach to a Therapy of 5–Oxoprolinuria.

COMPOSITION AND METHOD FOR WHITENING SKIN

This invention was made with government support under grant number R-814125 awarded by the U.S. Environmental Protection Agency. The government has certain rights in the invention.

This is a continuation-in-part of application Ser. No. 07/832,094, filed Feb. 6, 1992, now abandoned.

BACKGROUND OF THE INVENTION

The invention relates to compositions and methods for the whitening of skin and hair.

U.S. Pat. No. 4,990,330 discloses compositions for topical use having melanin synthesis-inhibiting activity comprising kojic acid or its esters and at least one compound selected from the group consisting of azelaic acid, tropolone, oipoic acid, sorbic acid, glucosamine, derivative of glucosamine, tunicamycin, deoxynojirimycin, glutathione, cysteine, hydroquinone, derivative of hydroquinone, dehydroacetic acid, chelidonic acid and lipoamide. Such compositions are disclosed as having excellent human skin-whitening and anti-suntan effects.

OBJECT OF THE INVENTION

It is an object of the invention to provide a novel, efficient, and safe way of whitening skin and hair in mammals and inhibiting the pigmenting effects of exposure to the sun.

Another object of the invention is to provide novel compositions to effect such whitening and inhibiting of sun-mediated pigmentation.

SUMMARY OF THE INVENTION

These and other objects are realized in accordance with the present invention pursuant to which there is administered to a mammal, preferably a human, an amount effective to achieve whitening of a compound which depletes glutathione, preferably a selective inhibitor of α-glutamyl synthetase and more preferably buthionine sulfoximine or cystamine.

Advantageously the material applied also contains hydroquinone or an alkyl or aralkyl ether of hydroquinone.

DETAILED DESCRIPTION OF THE INVENTION

Figure 1:
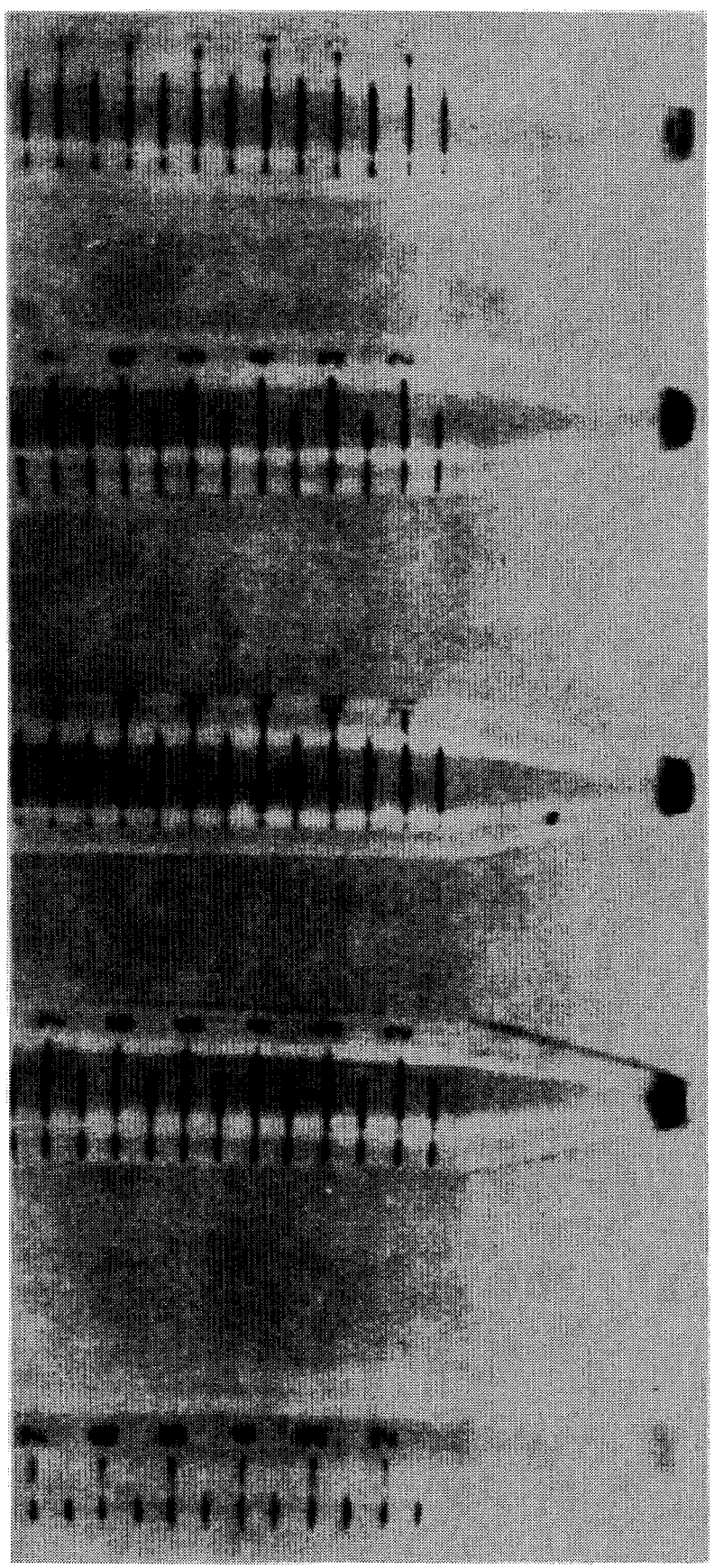
FIGS. 1-3 illustrate the application of hydroquinone and cystamine separately versus the application of a mixture of hydroquinone and cystamine to the back of a black hairless guinea pig.
Figure 2:
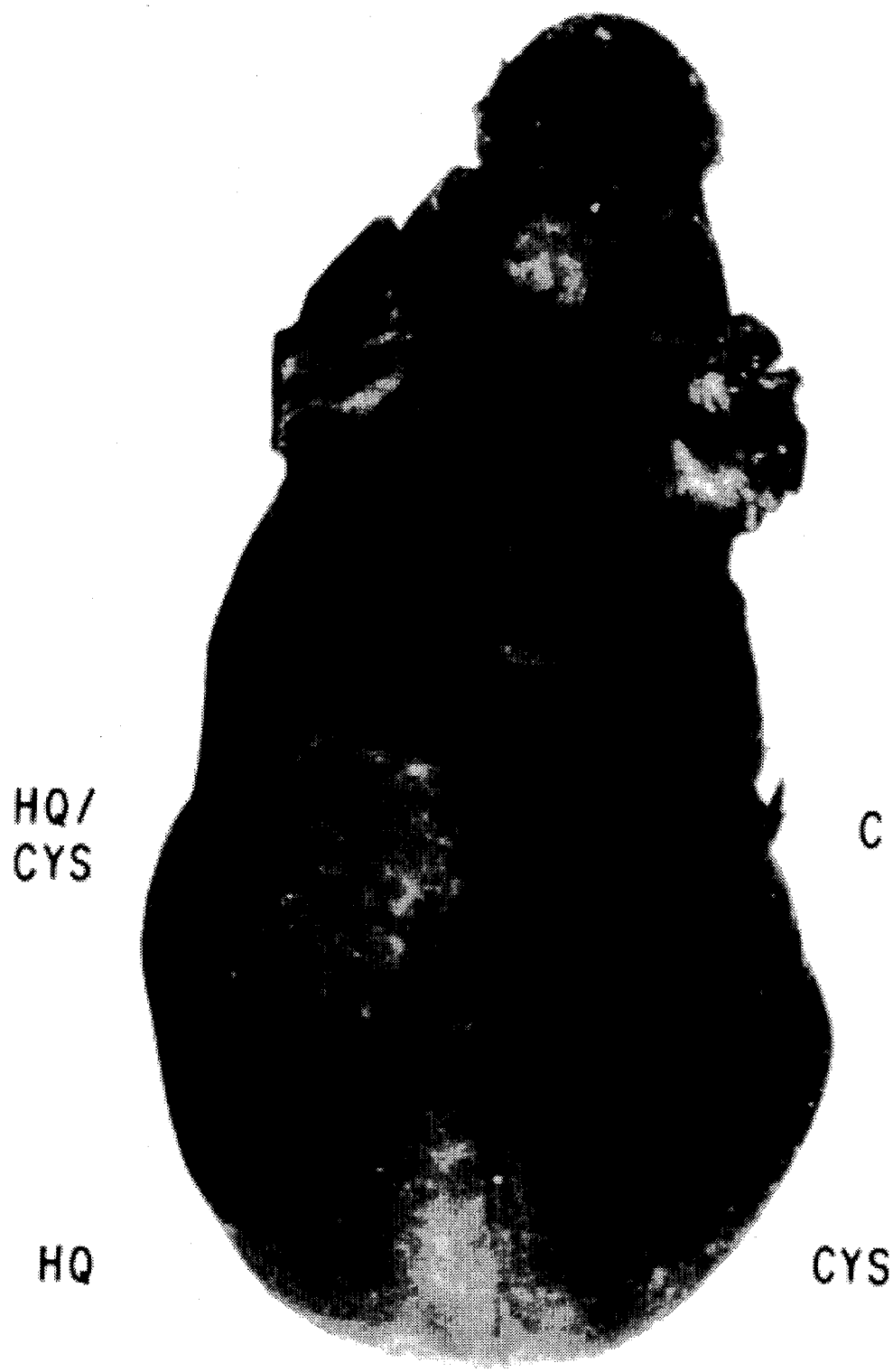
Figure 3:
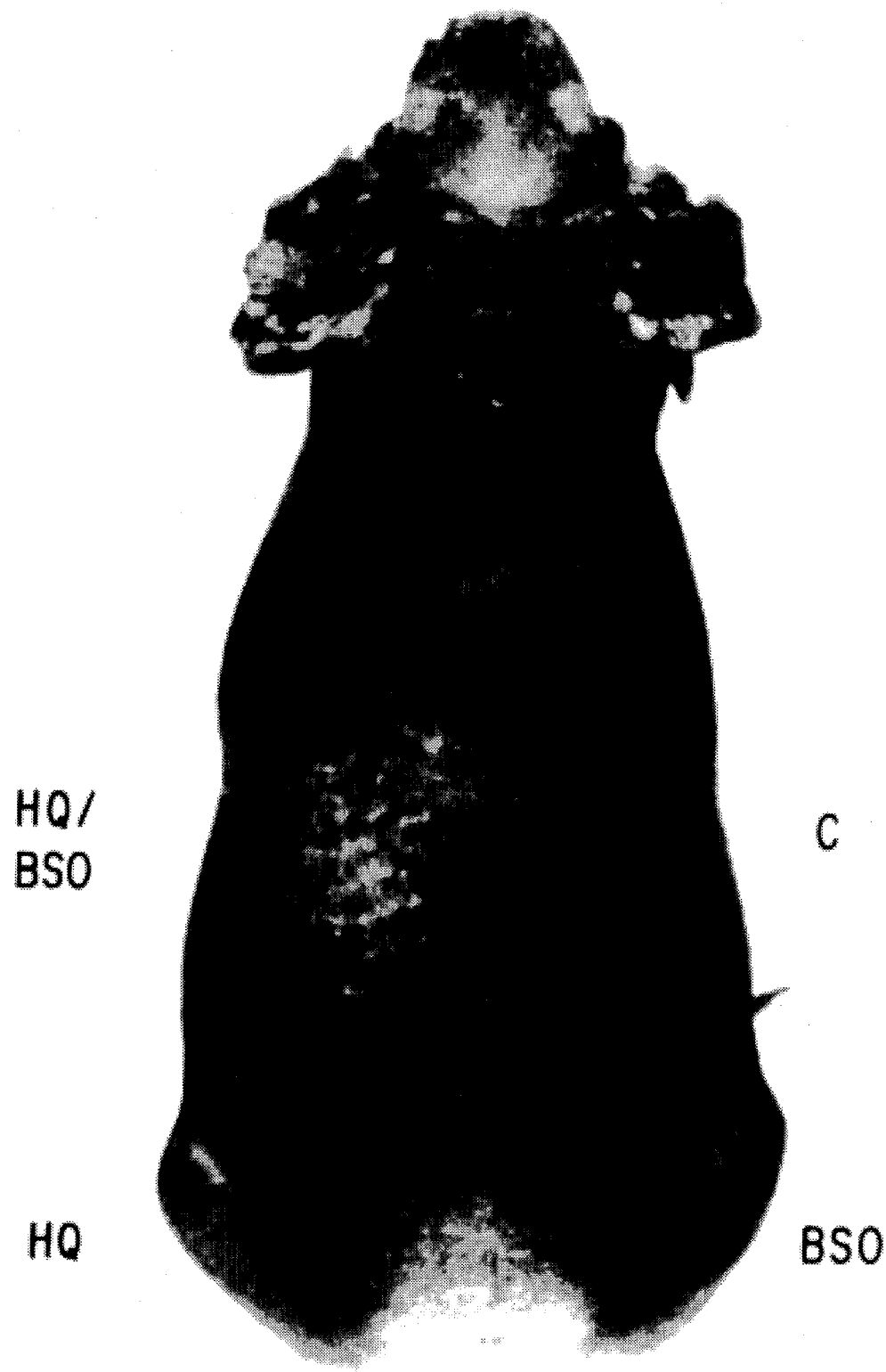

Buthionine sulfoximine is a known compound of the formula

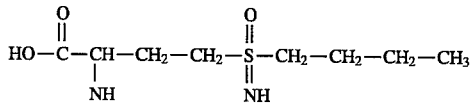

While it has been disclosed that it kills human melanoma cells grown in culture, it has not been disclosed that it has a whitening effect on human skin and hair.

In accordance with the invention, the inhibitor can be administered alone or preferably in combination with hydroquinone or an ether thereof, as specified hereinabove; hydroquinone and ethers thereof are known to have a whitening effect. Surprisingly, however, the combination of sulfoximine with hydroquinone or an ether thereof exhibits more than an additive effect.

In such joint administration, BSO primarily inhibits the enzyme "gamma glutamyl transpeptidase", whereas cystamine inhibits the enzyme "gamma glutamylcysteine synthetase". Both of these enzymes are essential for glutathione synthesis. Thus the buthionine sulfoximine or cystamine can be replaced by other compounds which deplete glutathione, particularly those which Selectively inhibit α-glutamyl synthetase.

The materials may be applied alone but are preferably administered dissolved or suspended in a carrier which may comprise water, conventional skin moisturizers and creams, and the like. Advantageously, such composition also contains an antioxidant, for which purpose ascorbic acid has been found especially useful.

The active materials can be administered in any manner but are preferably applied topically, e.g., by pouring or rubbing on the skin in the area sought to be whitened.

The selective inhibitor of α-glutamyl synthetase, e.g. buthionine sulfoximine, is advantageously applied in a carrier wherein it is present in a concentration of about 0.025 to 0.5 mole per liter.

As noted, the α-glutamyl synthetase inhibitor (a) is advantageously administered in conjunction with (b) hydroquinone or an alkyl or aralkyl ether thereof, e.g. the mono-benzyl ether.

When (b) is present, the weight ratio of (a):(b) ranges from about 10:1 to 1:10, advantageously from about 5:1 to 1:5 and preferably about 1:1.

When an antioxidant (c), such as ascorbic acid, is present desirably it is present in about 0.25 to 5% by weight, preferably about 1% by weight.

The invention will be further described in the following illustrative examples wherein all parts are by weight unless otherwise expressed.

Example 1

Mouse melanoma cells ($4 \times 10^6$) were grown in conventional cultures.

Portions were treated with:
i) nothing;
ii) $2 \times 10^{-7}$M melanocyte stimulating hormone (MSH) plus $10^{-4}$M isobutylmethylxanthine (IBMX);
iii) MSH and IBMX plus $1 \times 10^{-6}$ hydroquinone (H(HQ);
iv) MSH and IBMX plus $5 \times 10^{-6}$M buthionine sulfoximine (BSO):
v) MSH and IBMX plus HQ and BSO.

Following treatment, cells were collected by centrifugation and photographed. Results were as follows: (i) showed no color change and remained white; (ii) darkened considerably as expected, due to the known pigmenting effects of MSH and IBMX; (iii) and (iv) were slightly lighter than (ii); (v) was as white as (i) even though MSH and IBMX were present. The conclusions are that BSO in combination with HQ elicits a strong whitening effect on pigment-producing cells, preventing the induction of pigment by hormones. A further conclusion is that since MSH is known to be a key intermediary in ultraviolet light-induced pigmentation, it is implied that BSO and HQ also elicit inhibition of sun-mediated pigmentation.

Example 2

Ears and surrounding hair-bearing skin of living C57 black mice were rubbed daily with an aqueous solution containing 25% by weight of glycerol, 0.1 molar TRIS (trihydroxyaminomethane), buffered to p.H 6.8, to which there was added (A) nothing, (B) 4% by weight of hydroquinone, (c) 5% by weight of buthionine sulfoximine, and (D) 4% by weight of hydroquinone plus 5% by weight of buthionine sulfoximine. After 15 days (A) and (C) showed no depigmentation of the surrounding hairs where rubbed, (B) showed noticeable depigmentation and (D) showed marked depigmentation.

Example 3

The lower backs of living C57 Black mice, from which hair had been removed prior to treatment, were rubbed daily with Acid Mantle Creme (Sandoz Pharmaceuticals Corp.) containing aluminum sulfate, calcium acetate, cetearyl alcohol, glycerin, light mineral oil, methylparaben, purified water, sodium lauryl sulfate, synthetic beeswax, white petrolatum, white potato dextrin, ammonium hydroxide and citric acid, to which there was added (A) nothing (control), (B) 5% by weight buthionine sulfoximine (BSO), (C) 4% by weight hydroquinone (HQ), and (D) 5% by weight of buthionine sulfoximine plus 4% by weight of hydroquinone (BSO/HQ). Treatment was continued until new hair had grown out in the previously plucked regions (about 15 days). Approximately 100 new hairs from the treated areas were removed and scored under a microscope by two independent observers for the percentage of white hairs amongst the black hairs. (A) and (B) showed no white hairs, (C) showed about 2% white hairs, (D) showed about 14% white hairs. Thus BSO in combination with HQ is almost an order of magnitude more effective in eliciting whitening than either agent used alone.

Example 4

Cloudman S91 mouse melanoma cells were grown in culture in the presence of plain culture medium, or with the melanininducing hormone MSH ($10^{-7}$M), along with an MSH-enhancing agent, isobutylmethylxanthine (MIX $10^{-4}$M) and various additions of hydroquinone and/or cystamine as noted. The enzyme, tyrosinase, a rate-limiting enzyme in melanin biosynthesis, was assayed as an indicator of the melanogenesis pathway.

The results obtained are shown in the following table:

TABLE 1

Effects of Cystamine and Hydroquinone on MSH-Inducible Melanin Formation

| Additive to Culture Medium | Tyrosinase Activity (%) |
|---|---|
| MSH $10^{-7}$M + MIX $10^{-4}$M | 100% |
| MSH + MIX +: | |
| Hydroquinone ($10^{-6}$M) | 95% |
| Hydroquinone ($10^{-7}$M) | 129% |
| Cystamine ($10^{-5}$M) | 94% |
| Cystamine ($10^{-6}$M) | 116% |
| HQ ($10^{-6}$M/CYS $10^{-5}$M) | 50% |
| HQ ($10^{-6}$M/CYS $10^{-6}$M) | 77% |
| HQ ($10^{-7}$M/CYS $10^{-5}$M) | 76% |
| HQ ($10^{-7}$M/CYS $10^{-6}$M) | 116% |

Specifically, cystamine ($10^{-5}$M) in combination with hydroquinone ($10^{-6}$M) caused a 50% reduction in tyrosinase activity, whereas the compounds added alone had no effects on tyrosinase.

EXAMPLE 5

Composition and Method for Eliciting Whitening of Human Skin and for Inhibiting the Pigmenting Effects of Ultraviolet Light Acid Mantle Creme (Sandoz Pharmaceutical Corporation) (or other suitable carriers known to the art) containing 1–4% by weight hydroquinone and 1–5% by weight buthionine sulfoximine.

Directions: Apply daily until the desired whitening or prevention of sun tanning is achieved.

It will be appreciated that the instant specification and claims are set forth by way of illustration and not limitation, and that various modifications and changes may be made without departing from the spirit and scope of the present invention.

What is claimed is:

1. A skin-whitening and suntan-inhibiting composition comprising (a) a compound which depletes glutathione, said compound selected from buthionine sulfoximine and cystamine at a concentration in the range of 0.25 to 0.5M, and (b) hydroquinone or an alkyl or aralkyl ether of hydroquinone, in which the weight ratio of buthionine sulfoximine or cystamine to hydroquinone or ether thereof is from about 10:1 to 1:10.

2. A composition according to claim 1, wherein (a) is a selective inhibitor of α-glutamyl synthetase.

3. A composition according to claim 1, wherein (a) is buthionine sulfoximine.

4. A composition according to claim 1, wherein (a) is cystamine.

5. A composition according to claim 1, wherein (b) is hydroquinone or hydroquinone mono-benzyl ether.

6. A method of whitening skin which comprises applying to the skin an amount effective therefor of a composition according to claim 1.

7. The composition according to claim 1, wherein the weight ratio of buthionine sulfoximine or cystamine to hydroquinone or ether thereof is from about 5:1 to 1:5.

8. The composition according to claim 1, wherein the weight ratio of buthionine sulfoximine or cystamine to hydroquinone or ether thereof is about 1:1.

9. A skin-whitening and suntan-inhibiting composition comprising (a) a compound which depletes glutathione, said compound selected from buthionine sulfoximine at about 0.22M and cystamine at about 0.2M and (b) hydroquinone or an alkyl or aralkyl ether of hydroquinone, in which the weight ratio of buthionine sulfoximine to hydroquinone or ether thereof is about 5:4 or in which the weight ratio of cystamine to hydroquinone is about 3:4.

* * * * *